United States Patent
Mayorga et al.

(10) Patent No.: US 6,858,697 B2
(45) Date of Patent: Feb. 22, 2005

(54) STABILIZERS TO INHIBIT THE POLYMERIZATION OF SUBSTITUTED CYCLOTETRASILOXANE

(75) Inventors: Steven Gerard Mayorga, Oceanside, CA (US); Manchao Xiao, San Diego, CA (US); Thomas Richard Gaffney, Carlsbad, CA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 10/029,892

(22) Filed: Dec. 21, 2001

(65) Prior Publication Data

US 2003/0149213 A1 Aug. 7, 2003

(51) Int. Cl.[7] ................................................. C07F 7/21
(52) U.S. Cl. ........................ 528/31; 556/451; 556/460; 524/588
(58) Field of Search ........................... 528/31; 524/588; 556/451, 460

(56) References Cited

U.S. PATENT DOCUMENTS

| | | | | |
|---|---|---|---|---|
| 2,837,550 A | 6/1958 | Prober | .................... | 260/448.2 |
| 3,344,111 A | 9/1967 | Chalk | ........................ | 260/46.5 |
| 3,882,083 A | 5/1975 | Berger et al. | ............. | 260/46.5 |
| 3,998,865 A | 12/1976 | Siciliano et al. | ......... | 260/448.2 |
| 5,028,566 A | 7/1991 | Lagendijk | .................... | 437/238 |
| 5,118,735 A * | 6/1992 | Burnier | ........................ | 524/99 |
| 5,380,812 A | 1/1995 | Lutz et al. | .................... | 528/15 |
| 5,548,006 A | 8/1996 | Hirabayashi et al. | ......... | 524/82 |
| 6,368,359 B1 * | 4/2002 | Perry et al. | ..................... | 8/142 |
| 2004/0039219 A1 | 2/2004 | Chen et al. | | |

FOREIGN PATENT DOCUMENTS

JP          7145179          8/1999          ............. C07F/7/21

OTHER PUBLICATIONS

English language translation JP 07–145179.*
JP 07 145179 A: Patent Abstracts of Japan, vol. 1995, No. 09, Oct. 31, 1995.
XP–002233220: Derwent Publications Ltd., London, GB, AN 1980–10616C.
XP–002233221: Derwent Publications Ltd., London, GB, AN 1997–72075Y.
"User's Guide For: Glass Deposition With Teos," Dr. Arthur K. Hochberg, Schumacher, 1992.
Extrema® TOMCATS®, (Tetramethylcyclotetrasiloxane) Schumacher, 2000.
"Modeling of Low–Pressure Deposition of $SiO_2$ by Decomposition . . . ," Huppertz, et al, Schumacher, 1979.
"The Deposition of Silicon Dioxide Films at Reduced Pressure," Adams, et al, J. Electrochem Soc. 1979.
"Preparation of Device–quality $SiO_2$ Thin Films by Remote . . . ," G. Lucovsky, Adv. Mat. Optics . . . 1996.
"Deposition of Silicon Oxide Films From TEOS By Low . . . " G. Tochitani, et al, J. Vac. Sci. Tech. A, 1993.
"Properties of Silicon Dioxide Films Deposited at Low . . . ," S K. Ray, et al, J. Vac. Sci. Tech. B, 1992.
"Electron Cyclotron Resonance Microwave Discharge for Oxide . . . ," J. Electrochem Soc. 1992.
"Ion and Chemical Radical Effects on the Step Coverage . . . ," C.–P. Chang, et al. J. Appl. Phys. 67, 1990.
"Electron Cyclotron Resonance Microwave Discharge for Oxide . . . ," C.S. Pai, et al, J. Appl. Phys. 1993.
"User's Guide For: Undoped Glass, PSG, and BPSG Using. ," Schumacher, 1991.
"An Overview of the Polymerization of Cyclosiloxanes . . . ," J.E. McGrath, et al, ACS Symp , 1983.

* cited by examiner

*Primary Examiner*—Margaret G. Moore
(74) *Attorney, Agent, or Firm*—Rosaleen P. Morris-Oskanian

(57) ABSTRACT

The present invention is; (a) a process for stabilizing a cyclotetrasiloxane, such as 1,3,5,7-tetramethylcyclotetrasiloxane, against polymerization used in a chemical vapor deposition process for silicon oxides in electronic material fabrication comprising providing an effective amount of a neutral to weakly acidic polymerization inhibitor to such cyclotetrasiloxane; and (b) a composition of a cyclotetrasiloxane, such as 1,3,5,7-tetramethylcyclotetrasiloxane, stabilized against polymerization used in a chemical vapor deposition process as a precursor for silicon oxides in electronic material fabrication, comprising; such cyclotetrasiloxane and a neutral to weakly acidic polymerization inhibitor. A free radical scavenger can also be included in the process and composition.

28 Claims, No Drawings

STABILIZERS TO INHIBIT THE POLYMERIZATION OF SUBSTITUTED CYCLOTETRASILOXANE

BACKGROUND OF THE INVENTION

Silicon dioxide films have been used for some time in the fabrication of integrated circuits (IC) for semiconductor device manufacturing. There are many examples of the preparation of such thin films of $SiO_2$ in the open and patent literature. See, for example, the publications of the Schumacher Group, Air Products and Chemicals, Inc., e.g. User's Guide For: Glass Deposition with TEOS[1], and Extrema® TEOS (Tetraethyl Orthosilicate) Product Data Sheet[2]. See also, Modeling of Low-Pressure Deposition of $SiO_2$ by Decomposition of TEOS[3], and The Deposition of Silicon Dioxide Films at Reduced Pressure[4]. There are numerous journal articles that review various CVD techniques for the deposition of $SiO_2$ and the properties of thin films deposited using such techniques[5-9].

Early $SiO_2$ films were deposited by CVD oxidation of silane ($SiH_4$). New source materials were needed in order to maintain good step coverage as sub-micron patterned electronic devices were developed. Films deposited from tetra-ethylorthosilcate (TEOS) show superior step coverage properties compared to $SiH_4$[7]. TEOS is considered an industry standard source for the CVD preparation of $SiO_2$. TEOS is a volatile liquid, providing for efficient vapor delivery and general ease of handling. It is nonpyrophoric, and therefore, provides a significant safety advantage over silane. It produces dielectric films with excellent electrical and mechanical properties suitable for many device manufacturing applications.

The chemical 1,3,5,7-Tetramethylcyclotetrasiloxane (such as TOMCATS® siloxane available from Schumacher of Carlsbad, Calif.) is under development as a new source material for the CVD preparation of $SiO_2$ glass[10-11]. TOMCATS type siloxane is a high purity volatile liquid precursor chemical that is specifically designed to satisfy the critical demands of the semiconductor device manufacturing industry. Like TEOS, TOMCATS type siloxane can be used for the chemical vapor deposition of glasses and doped glasses for various dielectric film applications such as trench fill, interlevel dielectric, gate and thick oxide[2]. It provides similar safety advantages because of its non-pyrophoric and noncorrosive nature. The normal boiling points of TOMCATS type siloxane and TEOS are 135° C. and 168° C., respectively. The higher volatility of TOMCATS type siloxane allows it to be delivered at lower temperature or with higher efficiency at comparable temperature. Its deposition rate is 10 times that of TEOS at 600° C., with a deposition efficiency 3 times that of TEOS[2]. It is superior to silane and similar to TEOS in the conformality and step coverage of the resulting films[11-12].

In general, $SiO_2$ films deposited from TOMCATS type siloxane exhibit excellent mechanical and electrical properties. The films are dense with low carbon content and refractive index values comparable to thermal oxide. TOMCATS type siloxane is effective for low-pressure chemical vapor deposition (LPCVD) and as a liquid injection source for plasma enhanced chemical vapor deposition (PECVD). The later method utilizes plasmas rather than thermal energy to promote chemical reactions. TOMCATS type siloxane PECVD is typically run at lower temperature than LPCVD (400° C. vs. 500–600° C.).

Despite these advantages, TOMCATS type siloxane has experienced limited acceptance as a CVD source for the manufacturing of semiconductor devices. One disadvantage of TOMCATS type siloxane is its instability with respect to polymerization[13] when exposed to certain chemicals or process conditions. This results in a lower volatility liquid or gel that creates CVD process handling issues. TOMCATS type siloxane polymerization is catalyzed by acid or base. It has been observed in the present invention experimentally to be particularly sensitive to exposure to bases (see Examples 9–11 below).

Prolonged heating of TOMCATS type siloxane (Example 1) has also been shown experimentally in the present invention to promote polymerization. The degree of polymerization can be very minor, accounting for only several tenths of a percent. Under more severe conditions of prolonged exposure to elevated temperature or to certain acids or bases, substantial polymerization will occur, resulting in a highly viscous liquid or gel containing over 10% by weight of oligomeric or polymeric material.

Several references in the prior art relate to the stabilization of siloxane. Hirabayashi et al.[14] teach the use of a triazine or sulfide "control agent" to stabilize a mixture comprising an aliphatic unsaturated group, containing an organopolysiloxane compound, such as TOMCATS type siloxane, and a platinum group catalyst. Those inventors teach the use of the triazine or sulfide agent to give a mixture that is stable and resistant to premature gelation at room temperature and thus providing extended storage stability.

Lutz et al.[15] disclose the use of di- and trihydrocarbylphosphines which act as curing inhibitors for compositions comprising: (1) alkenyl radicals; (2) compounds containing silicon-bonded hydrogen atoms (e.g., TOMCATS type siloxane); and (3) a platinum group metal catalyst. Lutz et al. claim that the inhibitor functions by complexing with the platinum catalyst rendering it inactive for subsequent curing.

In a similar patent, Chalk[16] teaches the use of acrylonitrile type compounds that reduce the activity of the platinum catalyst deterring the copolymerization of various mixtures of polysiloxanes.

Berger et al.[17] propose the use of an ethylenically unsaturated isocyanurate which functions in a like manner to deactivate the Pt catalyst rendering a curable organopolysiloxane composition stable to premature gelation.

Endo et al.[18] teach the stabilization of cyclosiloxanes, such as TOMCATS type siloxane through the use of 1 to 20 weight % of polymethylpolysiloxanes, such as 1,1,1,3,5,5,5-heptamethyltrisiloxane.

The patent references cited all teach the use of various agents that in one manner or another inhibit the polymerization or co-polymerization of polysiloxanes for various applications in the silicon rubber industry. None of them specify or suggest applications as polymerization inhibitors for CVD sources in the semiconductor device manufacturing industry.

BRIEF SUMMARY OF THE INVENTION

The present invention is a process for stabilizing a substituted cyclotetrasiloxane against polymerization used in a chemical vapor deposition process for silicon oxides in electronic material fabrication comprising providing an effective amount of a neutral to weakly acidic polymerization inhibitor to a substituted cyclotetrasiloxane having the following formula:

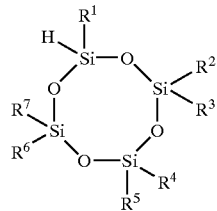

where $R^{1-7}$ are individually selected from the group consisting of hydrogen, a normal, branched or cyclic $C_{1-10}$ alkyl group, and a $C_{1-4}$ alkoxy group. The process can also include stabilization with a free radical scavenger.

The present invention is also a composition of substituted cyclotetrasiloxane stabilized against polymerization used in a chemical vapor deposition process as a precursor for silicon oxides in electronic material fabrication, comprising; (a) a substituted cyclotetrasiloxane having the following formula:

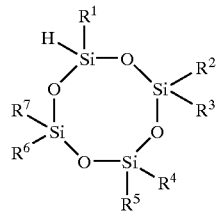

where $R^{1-7}$ are individually selected from the group consisting of hydrogen, a normal, branched or cyclic $C_{1-10}$ alkyl group, and a $C_{1-4}$ alkoxy group, and (b) a neutral to weakly acidic polymerization inhibitor. The composition can also include a free radical scavenger.

DETAILED DESCRIPTION OF THE INVENTION

The chemical 1,3,5,7-tetramethylcyclotetrasiloxane (such as TOMCATS® siloxane available from Schumacher of Carlsbad, Calif.) is used as a precursor for the chemical vapor deposition (CVD) of $SiO_2$ for semiconductor device manufacturing. TOMCATS type siloxane is currently under evaluation by semiconductor device manufacturers for use as a CVD precursors for $SiO_2$ because of its ability to form high quality films with excellent electronic and mechanical properties. TOMCATS type siloxane is known to polymerize when subjected to extended periods of heating or upon exposure to certain chemicals. In this invention we disclose the use of various additives that inhibit the polymerization of TOMCATS type siloxane. The effective additives are either neutral or weakly acidic with pKa values ranging from 4.88 to 14.15. The low concentration of the additive does not significantly impact the overall product purity, nor is it anticipated to have a negative impact on the critical properties of the resulting films produced by CVD.

Therefore, an object of the present invention is to eliminate or inhibit the polymerization of TOMCATS type siloxane under typical CVD process conditions. These TOMCATS type siloxanes include substituted cyclotetrasiloxanes of the formula:

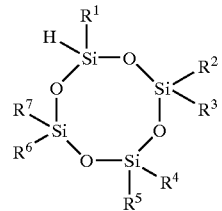

where $R^{1-7}$ are individually selected from the group consisting of hydrogen, a normal, branched or cyclic $C_{1-10}$ alkyl group, and a $C_{1-4}$ alkoxy group.

This is done through the use of additives that inhibit the polymerization of TOMCATS type siloxane under conditions that would normally favor polymerization. The present invention demonstrates that certain additives are effective at inhibiting polymerization, such as 2,4-pentanedione, 1-hexanoic acid, glycerol, acetic anhydride and 1,1,1,5,5,5-hexamethyltrisiloxane. Inhibitors contemplated by the present invention include: β-diketones, such as $RC(O)CH_2C(O)R$; aliphatic carboxylic acids or dicarboxylic acids, such as RCOOH or HOOC—$(CH_2)_n$—COOH in which $1 \leq n \leq 8$; phenols, such as $C_6R_{(6-n)}(OH)_n$, in which $1 \leq n \leq 5$; polyols, such as $CH_2X(CHX)_nCH_2X$, in which X=H or OH but at least one X=OH and $1 \leq n \leq 8$; anhydrides, such as $RCH_2$—C(O)—O—C(O)—$CH_2R$; and hydrodosiloxanes, such as $R_3Si$—(O—$SiR_2)_n$—$OSiR_3$, in which $0 \leq n \leq 8$.R, as used above, is individually selected from the group consisting of hydrogen, and a normal, branched or cyclic $C_{1-10}$ alkyl group.

Comparative data are also included (Example 8 and Table 1) which establish that 1,1,1,3,5,5,5-heptamethyltrisiloxane is an effective additive that deters polymerization when present at concentrations well below that described in the prior art[18]. In embodiments wherein one or more of the inhibitors is 1,1,1,3,5,5,5-heptamethyltrisiloxane, the amount of 1,1,1,3,5,5,5-heptamethyltrisiloxane may be less than 1% by volume. Alternatively, in embodiments wherein one or more inhibitors are 1,1,1,3,5,5,5-hexamethyltrisiloxane, the amount of 1,1,1,3,5,5,5-hexamethyltrisiloxane may be less than 1% by volume. These additives are collectively characterized as neutral to weakly acidic. The additives identified herein contain only carbon, oxygen, hydrogen and silicon, as in the latter case of the siloxanes, which give rise to volatile decomposition products such as $H_2O$ and $CO/CO_2$ in the CVD process. Furthermore, the additives were found to be effective at low enough concentrations, such that they do not significantly impact the overall purity of TOMCATS type siloxane.

Additional additives constituting free radical scavengers can also be added to the substituted cyclotetrasiloxanes. TOMCATS type siloxanes are sensitive to oxygen at elevated temperatures. TOMCATS type siloxanes react with oxygen forming oligomeric and polymeric species at temperatures equal to or greater than 60° C. This is significant because oxygen is commonly used as the oxidizing gas in plasma enhanced chemical vapor deposition (PECVD) processes for the deposition of $SiO_2$ films from TOMCATS type siloxane. These scavengers work by deterring chemical reactions that proceed by a free-radical reaction pathway. The free radical scavengers contemplated as $O_2$-stabilizers are 2,6-di-tert-butyl-4-methyl phenol (or BHT for butylhydroxytoluene), 2,2,6,6-tetramethyl-1-piperidinyloxy (TEMPO), 2-tert-butyl-4-hydroxyanisole, 3-tert-butyl-4-hydroxyanisole, propyl ester 3,4,5-trihydroxy-benzoic acid, 2-(1,1-dimethylethyl)-1,4-benzenediol, diphenylpicrylhydrazyl, 4-tert-butylcatechol, N-methylaniline, p-methoxydiphenylamine, diphenylamine, N,N'-diphenyl-p-phenylenediamine, p-hydroxydiphenylamine, phenol, octadecyl-3-(3,5-di-tert-butyl-4-hydroxyphenyl)propionate, tetrakis(methylene(3,5-di-tert-butyl)-4-hydroxy-hydrocinnamate)methane, phenothiazines, alkylamidonoisoureas, thiodiethylene bis(3,5,-di-tert-butyl-4-hydroxy-hydrocinnamate, 1,2,-bis(3,5-di-tert-butyl-4-hydroxyhydrocinnamoyl)hydrazine, tris(2-methyl-4-hydroxy-5-tert-butylphenyl)butane, cyclic neopentanetetrayl bis(octadecyl phosphite), 4,4'-thiobis(6-tert-butyl-m-cresol), 2,2'-methylenebis(6-tert-butyl-p-cresol), oxalyl bis(benzylidenehydrazide) and naturally occurring antioxidants such as raw seed oils, wheat germ oil, tocopherols and gums.

To attain the object of the present invention to eliminate or inhibit the polymerization of TOMCATS type siloxane under typical CVD process conditions, a standard laboratory test was established with the intent of accelerating the normal polymerization process. The accelerated aging test is meant to simulate the normal course of gradual polymerization that would typically occur over a more protracted period of time. This test, which consists of exposing a sealed quartz ampoule of TOMCATS type siloxane to elevated temperature for 5 days, is referred to in the present document as the "accelerated aging test". These conditions are understood to be considerably more severe than TOMCATS type siloxane would be subjected to in a typical CVD process. In a typical accelerated aging test, the ampoule is loaded with 3.0–7.0 ml of TOMCATS type siloxane and possibly an additive to inhibit polymerization. The TOMCATS type siloxane/additive mixture is cooled in a liquid nitrogen bath. Then, the atmosphere above the TOMCATS type siloxane is evacuated for 5 minutes. The neck of the quartz ampoule is subsequently sealed using a hydrogen/oxygen torch. The sealed ampoule is placed in an oven and held at 120° C. for 5 days. The ampoule is removed and allowed to cool to room temperature. Its contents are analyzed by gas chromatograph (GC) to measure the degree of polymerization.

The degree of polymerization is measured quantitatively by GC. This technique is very sensitive to detecting the onset of polymerization as evidenced by the formation of higher molecular weight species with longer retention times than the parent TOMCATS type siloxane peak. TOMCATS type siloxane samples that are determined to be of "high viscosity" by visual inspection are not routinely run on the GC. The oligomeric or polymeric siloxanes tend to irreversibly contaminate the stationary phase of the GC column due to their low solubility and low volatility. Such samples are qualitatively described in the present invention to have greater than 10 wt. % polymer, consistent with previous observations.

The polymerization of cyclical polysiloxanes is known to be catalyzed by either acid or base. Laboratory observations suggest that the polymerization of TOMCATS type siloxane is particularly sensitive to exposure to bases such as ammonia ($NH_3$) or ammonium hydroxide ($NH_4OH$). The result of exposure of TOMCATS type siloxane to base is described in Examples 9–11. In general, additives which are neutral to weakly acidic in low concentration were found to be effective at inhibiting polymerization. Weakly acidic additives, with pKa values ranging from 4.88 to 14.15 substantially minimized the degree of TOMCATS type siloxane polymerization. This is illustrated in Examples 2–4 and 6. Similarly, acetic anhydride, which is neutral on an acid-base scale, was also shown to inhibit polymerization as shown in Example 5. The additives were generally found to be effective over the concentration range of 100–1000 ppm (0.01–0.10%). This additive concentration is low enough such that it does not significantly impact the overall purity of the chemical relative to the additive-free source material. None of the additives contain nitrogen that is believed to have a detrimental impact on the quality of the resulting CVD films. The additives described in this invention form solutions with TOMCATS type siloxane at the tested concentrations. In addition, these additives are not anticipated to have a detrimental impact on the overall CVD process by virtue of their concentration and their chemical and physical characteristics.

EXAMPLE 1

Blank

In general a one or two blanks (additive-free TOMCATS type siloxane) were run for every set of stability experiments described in this invention. Several different batches of TOMCATS type siloxane source material were used. For the sake of clarity, all the results from the blank experiments were included in this example. The volume of the ampoules used for these tests was typically 80–90 ml. The quartz ampoules were routinely cleaned by rinsing with distilled water, then with reagent grade acetone. The rinsed ampoules were placed into a drying oven at 175° C. for a minimum of 4 hours. The dry ampoules were removed from the oven and used while still warm. 3.0–7.0 ml of TOMCATS type siloxane were loaded into each ampoule. Teflon valves were attached to the open end of the ampoules, and the TOMCATS type siloxane was cooled by immersing the end of the ampoules into a liquid nitrogen bath. The air was removed from the ampoules by subjecting them to vacuum for 5 minutes. The ampoules were sealed at the neck using a hydrogen/oxygen torch. The sealed ampoules were placed in a nitrogen-purged oven held at a constant temperature of 120° C. for 5 days. After 5 days the ampoules were removed from heat and allowed to cool to room temperature. If the samples were deemed to be highly viscous or solid by visual inspection they were not analyzed by GC, but instead they were assigned a degree of polymerization of ">10 wt. %." The value of >10 wt. % was based on GC analysis of previous samples that had undergone a similar viscosity increase. Again, GC analysis was not carried out for extensively polymerized samples because high levels of polymer tended to irreversibly contaminate the GC column. The blank TOMCATS type siloxane samples described in this example showed an increase in polymerization ranging from 0.18 wt % to >10 wt. %. The results are summarized in Table 1.

EXAMPLE 2

Spike of 100 ppm of 2,4-pentanedione

In a typical experiment 0.50 microliters of 2,4-pentanedione was added to an ampoule previously cleaned and dried as described in Example 1. To this ampoule 5.0 ml of TOMCATS type siloxane was added, taking care to rinse down any residual 2,4-pentanedione liquid that remained adhered to the inner wall of the ampoule. The ampoule thus prepared contained TOMCATS type siloxane with 100 ppm by volume of 2,4-pentanedione. The ampoule was sealed and heated for 5 days at 120° C. as described in Example 1. There was no detectable change in the viscosity, color or clarity of the TOMCATS type siloxane sample by visual inspection after the completion of the accelerated aging test as compared to the pristine sample prior to testing. Similar tests were done on 3.0 ml to 7.0 ml samples of TOMCATS type siloxane spiked with 100 ppm of 2,4-pentanedione additive. In each case there was no detectable visible changes in the sample after testing. These samples showed an increase in polymerization ranging from no increase to 0.35 wt. %. The results are summarized in Table 1.

EXAMPLE 3

Spike of 1000 ppm of 2,4-pentanedione

In a typical experiment 5.0 microliters of 2,4-pentanedione was added to an ampoule previously cleaned and dried as described in Example 1. To this ampoule 5.0 ml of TOMCATS type siloxane was added, taking care to rinse down residual 2,4-pentanedione liquid that remained adhered to the inner wall of the ampoule. The ampoule thus prepared contained TOMCATS type siloxane with 1000 ppm by volume of 2,4-pentanedione. The ampoule was sealed and heated for 5 days at 120° C. as described in Example 1. There was no detectable change in the viscosity, color or clarity of the TOMCATS type siloxane sample by visual inspection after the completion of the accelerated aging test as compared to the pristine sample prior to testing. Similar tests were done on 3.0 ml to 7.0 ml samples of TOMCATS type siloxane spiked with 100 ppm of 2,4-pentanedione additive. In each case there was no detectable visible changes in the sample after testing. These samples showed an increase in polymerization ranging from 0.11 wt. % to 0.30 wt. %. The results are summarized in Table 1.

EXAMPLE 4

Spike of 100–1000 ppm of 1-hexanoic Acid 0.70 microliters and 3.0 microliters of 1-hexanoic acid were added to each of two ampoules previously cleaned and dried as described in Example 1. 7.0 ml and 3.0 ml of TOMCATS type siloxane were added to each of these ampoules, respectively, taking care to rinse down residual 1-hexanoic acid liquid that remained adhered to the inner wall of the ampoules. The ampoules thus prepared contained TOMCATS type siloxane with 100 ppm (vol.) and 1000 ppm (vol.) of 1-hexanoic acid, respectively. The ampoules were sealed and heated for 5 days at 120° C. as described in Example 1. There were no detectable changes in the viscosity, color or clarity of the TOMCATS type siloxane sample by visual inspection after the completion of the accelerated aging test as compared to the pristine sample prior to testing. The GC data showed an increase in polymerization of 0.08 wt. % and 2.84 wt. % for the TOMCATS type siloxane samples spiked with 100 ppm and 1000 ppm of additive, respectively. Results are summarized in Table 1.

EXAMPLE 5

Spike of 100–1000 ppm of Acetic Anhydride 0.50 microliters and 5.0 microliters of acetic anhydride were added to each of two ampoules previously cleaned and dried as described in Example 1. 5.0 ml of TOMCATS type siloxane was added to each ampoule taking care to rinse down residual acetic anhydride liquid that remained adhered to the inner wall of the ampoules. The ampoules thus prepared contained TOMCATS type siloxane with 100 ppm (vol.) and 1000 ppm (vol.) of acetic anhydride, respectively. The ampoules were sealed and heated for 5 days at 120° C. as described in Example 1. There were no detectable changes in the viscosity, color or clarity of the TOMCATS type siloxane sample by visual inspection after the completion of the accelerated aging test as compared to the pristine sample prior to testing. These tests were repeated twice more for each additive concentration. The GC data showed an increase in polymerization of 0.08 wt. % to 0.38 wt. % for the TOMCATS type siloxane samples spiked with 100 ppm of additive; and an increase in polymerization of 0.14 wt. % to 0.38 wt. % for the TOMCATS type siloxane samples spiked with 1000 ppm of additive. The results are summarized in Table 1.

EXAMPLE 6

Spike of 100 ppm of Glycerol 0.61 mg (0.48 microliters) of glycerol was added to an ampoule previously cleaned and dried as described in Example 1. 5.0 ml of TOMCATS type siloxane was added to the ampoule taking care to rinse down residual glycerol liquid that remained adhered to the inner wall of the ampoule. The ampoule thus prepared contained TOMCATS type siloxane with 100 ppm (vol.) of glycerol. The ampoule was sealed and heated for 5 days at 120° C. as described in Example 1. There was no detectable change in the viscosity, color or clarity of the TOMCATS type siloxane sample by visual inspection after the completion of the accelerated aging test as compared to the pristine sample prior to testing. The GC data showed an increase in polymerization of 0.12 wt. % for the TOMCATS type siloxane samples spiked with 100 ppm of additive. The results are summarized in Table 1.

EXAMPLE 7

Spike of 1,1,1,5,5,5-hexamethyltrisiloxane 3.0 microliters and 30 microliters of 1,1,1,5,5,5-hexamethyltrisiloxane were added to each of two ampoules previously cleaned and dried as described in Example 1. 3.0 ml of TOMCATS type siloxane was added to each ampoule taking care to rinse down residual 1,1,1,5,5,5-hexamethyltrisiloxane liquid that remained adhered to the inner wall of the ampoules. The ampoules thus prepared contained TOMCATS type siloxane with 1000 ppm and 10,000 ppm (vol.) of 1,1,1,5,5,5-hexamethyltrisiloxane, respectively. The ampoules were sealed and heated for 5 days at 120° C. as described in Example 1. There were no detectable changes in the viscosity, color or clarity of the TOMCATS type siloxane sample by visual inspection after the completion of the accelerated aging test as compared to the pristine sample prior to testing. The GC data showed an increase in polymerization of 0.20 wt. % and 0.66 wt. % for the TOMCATS type siloxane samples spiked with 1000 ppm and 10,000 ppm of additive, respectively. The results are summarized in Table 1.

EXAMPLE 8

Spike of 1,1,1,3,5,5,5-heptamethyltrisiloxane 0.30, 30 and 150 microliters of 1,1,1,3,5,5,5-heptamethyltrisiloxane were added to each of three ampoules previously cleaned and dried as described in Example 1. 3.0 ml of TOMCATS type siloxane was added to each ampoule taking care to rinse down residual 1,1,1,3,5,5,5-heptamethyltrisiloxane liquid that remained adhered to the inner wall of the ampoules. The ampoules thus prepared contained TOMCATS type siloxane with 100 ppm (vol.), 10,000 ppm (vol.) and 50,000 ppm (vol.) of 1,1,1,3,5,5,5-heptamethyltrisiloxane, respectively. The ampoules were sealed and heated for 5 days at 120° C. as described in Example 1. There were no detectable changes in the viscosity, color or clarity of the TOMCATS type siloxane sample by visual inspection after the completion of the accelerated aging test as compared to the pristine sample prior to testing. The GC data showed an increase in polymerization of up to 0.33 wt. % for the TOMCATS type siloxane samples spiked with the aforementioned levels of additive. Results are summarized in Table 1.

Example 8 is a comparative example in which accelerated aging tests are carried out on a sample of TOMCATS type siloxane spiked with various levels of 1,1,1,3,5,5,5-heptamethyltrisiloxane ranging from 100 ppm to 50,000 ppm (5%) by weight. This example illustrates that the heptamethyltrisiloxane is effective at inhibiting polymerization at concentrations below the 1 wt. % lower limit claimed by Endo et. al[18].

EXAMPLE 9

Spike of 15 ppm and 150 ppm of Anhydrous Ammonia

Two 100 ml Pyrex Schlenk flasks equipped with side arms and stopcocks were connected to a vacuum line. The flasks were thoroughly dried by heating intermittently with a hydrogen/oxygen torch while pulling a vacuum on the flasks through the side arms. The flasks were isolated from the vacuum line by closing the stopcock valves on the side arms. 5.0 ml of TOMCATS type siloxane was introduced into each of the flasks by injection with a syringe through the rubber septum on the top of the flask. The two flasks were back-filled with dry nitrogen gas to ambient pressure. 0.10 ml and 1.0 ml of anhydrous ammonia gas were introduced into each of the two flasks. The flasks thus prepared contained TOMCATS type siloxane spiked with 15 ppm and 150 ppm ammonia by weight, respectively. The flasks were allowed to stand at room temperature for 24 hours. One ml aliquots of TOMCATS type siloxane were removed from each of the two flasks by syringe 2 hours and 20 hours after the beginning of the test. The four samples were analyzed by GC to determine the extent of polymerization. The sample of TOMCATS type siloxane spiked with 15 ppm of $NH_3$ showed increases in polymerization of 0.11% and 0.18% after 2 hours and 20 hours, respectively. The sample of TOMCATS type siloxane spiked with 150 ppm of $NH_3$ showed increases in polymerization of 0.10% and 0.17% after 2 hours and 20 hours, respectively. The results are summarized in Table 2.

EXAMPLE 10

Siloxane/100 ppm of 2,4-pentanedione Spiked with 15 ppm and 150 ppm of Anhydrous Ammonia Two 100 ml Pyrex Schlenk flasks were dried by heating on the vacuum line as described in Example 9. 0.5 microliters of 2,4-pentanedione was added to each of the flasks using a 1.0 microliter syringe. 5.0 ml of TOMCATS type siloxane was subsequently introduced into each of the flasks by injection with a syringe through the rubber septum on the top of the flask. The TOMCATS type siloxane was added in such a manner to ensure that residual 2,4-pentanedione was thoroughly rinsed down from the sides of the flask. The two flasks were back-filled with dry nitrogen gas to ambient pressure. 0.10 ml and 1.0 ml of anhydrous ammonia gas were introduced into each of the two flasks. The two flasks thus prepared contained 100 ppm of 2,4-pentanedione in TOMCATS type siloxane spiked with 15 ppm and 150 ppm ammonia by weight, respectively. The flasks were allowed to stand at room temperature for 24 hours. One ml aliquots were removed from each of the two flasks by syringe 2 hours and 20 hours after the beginning of the test. The four samples were analyzed by GC to determine the extent of polymerization. The sample of TOMCATS type siloxane spiked with 15 ppm of $NH_3$ showed 0.08% polymerization after 2 hours and 20 hours, respectively. The sample of TOMCATS type siloxane spiked with 150 ppm of $NH_3$ showed 0.07% and 0.09% polymerization after 2 hours and 20 hours, respectively. The results are summarized in Table 2.

EXAMPLE 11

Exposure to 1.0 wt. % Anhydrous Ammonia 5.0 ml of TOMCATS type siloxane was added to each of two ampoules previously cleaned and dried as described in Example 1. Each of the ampoules was equipped with a side arm capped with a rubber septum. The TOMCATS type siloxane samples in the ampoules were cooled by submersion in a liquid nitrogen bath. The air was removed from the ampoules by exposing to vacuum conditions for 5 minutes. At this time the ampoules were isolated from the vacuum and 72 ml of anhydrous ammonia gas (at ambient pressure) was injected through the rubber septa into each of the ampoules. This corresponds to 1.0 wt. % $NH_3$–99.0 wt. % TOMCATS type siloxane. The ampoules were sealed under vacuum with a torch as described in Example 1. The liquid nitrogen was removed and the TOMCATS type siloxane/ammonia mixtures were allowed to slowly warm to room temperature. The liquid was noticed to be quite viscous within 30 minutes after warming to room temperature. The ampoules were heated for 5 days at 120° C. as described in Example 1. The ampoules were removed from the oven and allowed to cool to room temperature. The TOMCATS type siloxane liquid had become highly viscous, similar in consistency to molasses. The samples were determined to be too polymerized to analyze by GC and were assigned a degree of polymerization of >10 wt. %.

TABLE 1

TOMCATS type siloxane Accelerated Aging Tests Using Various Additives

| Ex. Run # | Additive and Concentration by volume | pKa of additive | TOMCATS type siloxane purity (wt. %) pre-test | TOMCATS type siloxane purity (wt. %) post-test | Increase in polymerization (wt. %) |
|---|---|---|---|---|---|
| Run #1 (a) | Blank (no additive) | N.A | 99.80 | <90% | >10 |
| Run #1 (b) | Blank (no additive) | N.A | 99.80 | <90% | >10 |
| Run #1 (c) | Blank (no additive) | N.A | 99.80 | 99.54 | 0.26 |
| Run #1 (d) | Blank (no additive) | N.A | 99.80 | 99.61 | 0.19 |
| Run #1 (e) | Blank (no additive) | N.A | 99.21 | 90.52 | 8.69 |
| Run #1 (f) | Blank (no additive) | N.A | 99.62 | 99.44 | 0.18 |
| Run #1 (g) | Blank (no additive) | N.A | 99.62 | <90% | >10 |
| Run #1 (h) | Blank (no additive) | N.A | 99.54 | 98.00 | 1.54 |
| Run #2 (a) | 100 ppm 2,4-pentanedione | 9.0 | 99.80 | 99.76 | 0.03 |
| Run #2 (b) | 100 ppm 2,4-pentanedione | 9.0 | 99.62 | 99.55 | 0.06 |
| Run #2 (c) | 100 ppm 2,4-pentanedione | 9.0 | 99.62 | 99.26 | 0.35 |
| Run #2 (d) | 100 ppm 2,4-pentanedione | 9.0 | 99.62 | 99.35 | 0.26 |
| Run #2 (e) | 100 ppm 2,4-pentanedione | 9.0 | 99.54 | 99.54 | 0.00 |
| Run #2 (f) | 100 ppm 2,4-pentanedione | 9.0 | 99.54 | 99.53 | 0.00 |
| Run #3 (a) | 1000 ppm 2,4-pentanedione | 9.0 | 99.80 | 99.40 | 0.30 |
| Run #3 (b) | 1000 ppm 2,4-pentanedione | 9.0 | 99.62 | 99.40 | 0.12 |
| Run #3 (c) | 1000 ppm 2,4-pentanedione | 9.0 | 99.62 | 99.41 | 0.11 |
| Run #4 (a) | 100 ppm 1-hexanoic acid | 4.88 | 99.80 | 99.71 | 0.08 |
| Run #4 (b) | 1000 ppm 1-hexanoic acid | 4.88 | 99.80 | 96.86 | 2.84 |
| Run #5 (a) | 100 ppm acetic anhydride | N.A | 99.62 | 99.53 | 0.08 |
| Run #5 (b) | 100 ppm acetic anhydride | N.A | 99.62 | 99.47 | 0.14 |
| Run #5 (c) | 100 ppm acetic anhydride | N.A | 99.62 | 99.23 | 0.38 |
| Run #5 (d) | 1000 ppm acetic anhydride | N.A | 99.62 | 99.38 | 0.14 |
| Run #5 (e) | 1000 ppm acetic anhydride | N.A | 99.62 | 99.30 | 0.22 |
| Run #5 (f) | 1000 ppm acetic anhydride | N.A | 99.62 | 99.14 | 0.38 |
| Run #6 (a) | 100 ppm glycerol | 14.15 | 99.62 | 99.49 | 0.12 |
| Run #7 (a) | 1000 ppm 6MTS* | | 99.80 | 99.50 | 0.20 |
| Run #7 (b) | 10,000 ppm 6MTS* | | 99.80 | 98.14 | 0.66 |
| Run #8 (a) | 100 ppm 7MTS** | | 99.80 | 99.46 | 0.33 |
| Run #8 (b) | 10,000 ppm 7MTS** | | 99.80 | 98.73 | 0.07 |
| Run #8 (c) | 50,000 ppm 7MTS** | | 99.80 | 95.46 | 0 |

*1,1,1,5,5,5-hexamethyltrisiloxane
**1,1,1,3,5,5,5-heptamethyltrisiloxane

TABLE 2

The Effect of 2,4-Pentanedione to Limit the Polymerization of TOMCATS type siloxane Containing Low Levels of Anhydrous Ammonia Gas

| Ex. Run # | NH₃ concentration by weight | 2,4-pentanedione conc. by weight | % Polymerization after 2 hours at 25° C. | % Polymerization after 20 hours at 25° C. |
|---|---|---|---|---|
| Run #9 (a) | 15 ppm | none | 0.11 | 0.18 |
| Run #9 (b) | 150 ppm | none | 0.10 | 0.17 |
| Run #10 (a) | 15 ppm | 100 ppm | 0.08 | 0.08 |
| Run #10 (b) | 150 ppm | 100 ppm | 0.07 | 0.09 |

In-house experiments have established that TOMCATS type siloxane is sensitive to oxygen at elevated temperatures. TOMCATS type siloxane reacts with oxygen forming oligomeric and polymeric species at temperatures equal to or greater than 60° C. This is particularly important since oxygen is commonly used as the oxidizing gas in PECVD processes for the deposition of SiO$_2$ films from TOMCATS type siloxane. Data collected in the 22° C. to 120° C. range are shown in Table 3.

The preferred additive, 2,4-pentanedione, does not prevent the polymerization of TOMCATS type siloxane in the presence of oxygen. To address this reactivity TOMCATS type siloxane was spiked with low levels of chemicals which function as free radical scavengers, i.e., antioxidants. These scavengers work by deterring chemical reactions that proceed by a free-radical reaction pathway. The free radical scavengers investigated as O$_2$-stabilizers were 2,6-di-tert-butyl-4-methyl phenol (or BHT for butylhydroxytoluene) and 2,2,6,6-tetramethyl-1-piperidinyloxy (TEMPO). TOMCATS type siloxane was substantially more resistant toward O$_2$ when spiked with either one of these free radical scavengers. The addition of 50–500 ppm of BHT completely eliminated the reactivity of TOMCATS type siloxane toward oxygen at elevated temperature as shown by the series of tests run at 80° C. Another benefit is that BHT is free of atomic nitrogen which reportedly gives rise to undesirable basic film properties. TEMPO was also shown to be an effective O$_2$-stabilizer. Addition of 50–230 ppm of TEMPO to TOMCATS type siloxane reduced the degree of O$_2$-promoted polymerization by over 80% (Table 3).

These tests clearly established the benefit of the use of low levels of free radical scavengers to greatly reduce or eliminate the sensitivity of TOMCATS type siloxane to oxygen, thereby, reducing the likelihood of plugging problems occurring by the oxygen promoted polymerization of TOMCATS type siloxane. The scavengers/antioxidants contemplated for this utility include: 2,6-di-tert-butyl-4-methyl phenol, 2,2,6,6-tetramethyl-1-piperidinyloxy, 2-tert-butyl-4-hydroxyanisole, 3-tert-butyl-4-hydroxyanisole, propyl ester 3,4,5-trihydroxy-benzoic acid, 2-(1,1-dimethylethyl)-1,4-benzenediol, diphenylpicrylhydrazyl, 4-tert-butylcatechol, N-methylaniline, p-methoxydiphenylamine, diphenylamine, N,N'-diphenyl-p-phenylenediamine, p-hydroxydiphenylamine, phenol, octadecyl-3-(3,5-di-tert-butyl-4-hydroxyphenyl) propionate, tetrakis(methylene(3,5- di-tert-butyl)-4-hydroxy-hydrocinnamate)methane, phenothiazines, alkylamidonoisoureas, thiodiethylene bis(3,5,-di-tert-butyl-4-hydroxy-hydrocinnamate, 1,2,-bis(3,5-di-tert-butyl-4-hydroxyhydrocinnamoyl)hydrazine, tris(2-methyl-4-hydroxy-5-tert-butylphenyl)butane, cyclic neopentanetetrayl bis(octadecyl phosphite), 4,4'-thiobis(6-tert-butyl-m-cresol), 2,2'-methylenebis(6-tert-butyl-p-cresol), oxalyl bis(benzylidenehydrazide) and mixtures thereof. Naturally occurring antioxidants can also be used such as raw seed oils, wheat germ oils tocopherols and gums.

TABLE 3

TOMCATS type siloxane/Oxygen Compatibility Tests
Five day aging tests were conducted at 22° C., 60° C., 80° C., 90° ° C. and 120° C.
For all of these tests TOMCATS type siloxane containing 100 ppm of 2,4-pentanedione was exposed to 0.5 wt. % O$_2$.

| Ex. Run # | Temperature (° C.) | Free-Radical Scavenger | Scavenger Concentration (ppm) | % Polymerization* 1 day | 5 days |
|---|---|---|---|---|---|
| Run # 11 (a) | 120 | None | 0 | 7.1 | 7.9 |
| Run # 11 (b) | 90 | None | 0 | 6.8 | 7.0 |
| Run # 11 (c) | 80 | None | 0 | not collected | 5.1 |
| Run # 11 (d) | 60 | None | 0 | 1.7 | 6.8 |
| Run # 11 (e) | 22 | None | 0 | 0.0 | 0.0 |
| Run # 12 (a) | 80 | BHT | 50 | not collected | 0.10 |
| Run # 12 (b) | 80 | BHT | 100 | not collected | 0.03 |
| Run # 12 (c) | 80 | BHT | 200 | not collected | 0.04 |
| Run # 12 (d) | 80 | BHT | 500 | not collected | 0.05 |
| Run # 13 (a) | 80 | TEMPO | 50 | not collected | 0.82 |
| Run # 13 (b) | 80 | TEMPO | 100 | not collected | 0.82 |
| Run # 13 (c) | 80 | TEMPO | 230 | not collected | 0.88 |

EXAMPLE 12

Reactivity of Oxygen Spike of 100 ppm of 2,4-pentanedione 0.50 microliters of 2,4-pentanedione was added to an ampoule previously cleaned and dried as described in Example 1. The ampoule was equipped with a quartz side arm extension capped with a septum. To this ampoule 5.0 ml of TOMCATS type siloxane was added, taking care to rinse down any residual 2,4-pentanedione liquid that remained adhered to the inner wall of the ampoule. The ampoule thus prepared contained TOMCATS type siloxane with 100 ppm by volume of 2,4-pentanedione. The ampoule was cooled to liquid nitrogen temperature and evacuated to remove air. The ampoule was isolated from the vacuum and a pre-determined amount of oxygen was injected through the side arm. Two ampoules prepared in this manner were sealed and heated for 1 day at 120° C. as described in Example 1. Two additional ampoules prepared in like manner were heated for 5 days. These samples showed an average increase in polymerization of 7.1% and 7.9% after one day and after 5 days, respectively.

This set of tests was repeated at 90° C., 80° C., 60° C. and 22° C. Data were collected only after 5 days for the 80° C. test. Significant polymerization again occurred at 90° C., 80° C. and 60° C., but was absent at 22° C. The data are summarized in Table 3.

EXAMPLE 13

Reactivity of Oxygen Spike of 100 ppm of 2,4-pentanedione and 50–500 ppm of BHT 0.50 microliters of 2,4-pentanedione was added to an ampoule previously cleaned and dried as described in Example 1. The ampoule was equipped with a quartz side arm extension capped with a septum. 5.0 ml of TOMCATS type siloxane containing 50 ppm of dissolved BHT was added to the ampoule. The ampoule thus prepared contained TOMCATS type siloxane with 100 ppm by volume of 2,4-pentanedione and 50 ppm BHT. The ampoule was cooled to liquid nitrogen temperature and evacuated to remove air. The ampoule was isolated from the vacuum and a pre-determined amount of oxygen was injected through the side arm. Two ampoules prepared in this manner were sealed and heated for 5 days at 80° C. as described in Example 1. These duplicate samples showed an increase in polymerization of 0.05% and 0.15% for an average of 0.10%. The data are summarized in Table 3.

The above tests were repeated in duplicate using 100 ppm, 200 ppm and 500 ppm of BHT. Less than 0.05% polymerization increase was observed for each of these three levels of BHT additive.

EXAMPLE 14

Reactivity of Oxygen Spike of 100 ppm of 2,4-pentanedione and 50–230 ppm of 2,2,6,6-tetramethyl-1-piperidinyloxy (TEMPO)

0.50 microliters of 2,4-pentanedione was added to an ampoule previously cleaned and dried as described in Example 1. The ampoule was equipped with a quartz side arm extension capped with a septum. 5.0 ml of TOMCATS® containing 50 ppm of dissolved TEMPO was added to the ampoule. The ampoule thus prepared contained TOMCATS type siloxane with 100 ppm by volume of 2,4-pentanedione and 50 ppm TEMPO. The ampoule was cooled to liquid nitrogen temperature and evacuated to remove air. The ampoule was isolated from the vacuum and a pre-determined amount of oxygen was injected through the side arm. Two ampoules prepared in this manner were sealed and heated for 5 days at 80° C. as described in Example 1. These samples showed an increase in polymerization of 0.89% and 0.76% for an average of 0.82%. The data are summarized in Table 3.

The above tests were repeated in duplicate using 100 ppm and 230 ppm of TEMPO. TOMCATS type siloxane spiked with these levels of TEMPO underwent 0.82% and 0.88% increase in polymerization, respectively.

The present invention has been set forth with regard to several preferred embodiments, but the full scope of the present invention should be ascertained from the claims which follow.

What is claimed is:

1. A process for stabilizing a cyclotetrasiloxane against polymerization, the cyclotetrasiloxane having the following formula:

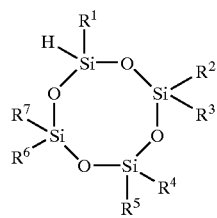

wherein R$^{1-7}$ are individually selected from the group consisting of hydrogen, a normal, branched or cyclic C$_{1-10}$ alkyl group, and a C$_{1-4}$ alkoxy group, the process comprising:

providing an effective amount of an inhibitor to the cyclotetrasiloxane wherein the inhibitor is selected from 2,4-pentanedione; 1-hexanoic acid; glycerol; acetic anhydride; β-diketones RC(O)CH$_2$C(O)R; aliphatic carboxylic acids RCOOH; aliphatic dicarboxylic acids HOOC—(CH$_2$)$_n$—COOH in which $1 \leq n \leq 8$; phenols C$_6$R$_{(6-n)}$(OH)$_n$ in which $1 \leq n \leq 5$; polyols CH$_2$X(CHX)$_n$CH$_2$X, in which X=H or OH but at least one X=OH and $1 \leq n \leq 8$; anhydrides RCH$_2$—C(O)—O—C(O)—CH$_2$R; hydrodosiloxanes R$_3$Si—(O—Si R$_2$)$_n$OSiR$_3$, in which $0 \leq n \leq 8$, all wherein R is individually selected from the group consisting of hydrogen, normal, branched or cyclic C$_{1-10}$ alkyl groups; and mixtures thereof.

2. The process of claim 1 including providing a free radical scavenger to said cyclotetrasiloxane.

3. The process of claim 2 wherein said free radical scavenger is selected from the group consisting of: 2,6-di-tert-butyl-4-methyl phenol, 2,2,6,6-tetramethyl-1-piperidinyloxy, 2-tert-butyl-4-hydroxyanisole, 3-tert-butyl-4-hydroxyanisole, propyl ester 3,4,5-trihydroxy-benzoic acid, 2-(1,1-dimethylethyl)-1,4-benzenediol, diphenylpicrylhydrazyl, 4-tert-butylcatechol, N-methylaniline, p-methoxydiphenylamine, diphenylamine, N,N'-diphenyl-p-phenylenediamine, p-hydroxydiphenylamine, phenol, octadecyl-3-(3,5-di-tert-butyl-4-hydroxyphenyl)propionate, tetrakis(methylene(3,5-di-tert-butyl)-4-hydroxy-hydrocinnamate)methane, phenothiazines, alkylamidonoisoureas, thiodiethylene bis(3,5,-di-tert-butyl-4-hydroxy-hydrocinnamate, 1,2,-bis(3,5-di-tert-butyl-4-hydroxyhydrocinnamoyl)hydrazine, tris(2-methyl-4-hydroxy-5-tert-butylphenyl)butane, cyclic neopentanetetrayl bis(octadecyl phosphite), 4,4'-thiobis(6-tert-butyl-m-cresol), 2,2'-methylenebis(6-tert-butyl-p-cresol), oxalyl bis(benzylidenehydrazide) and mixtures thereof.

4. The process of claim 3 wherein said 2,6-di-tert-butyl-4-methyl phenol is provided in an amount of 50–500 ppm (vol.).

5. The process of claim 3 wherein said 2,2,6,6-tetramethyl-1-piperidinyloxy is provided in an amount of 50–230 ppm (vol.).

6. A process for stabilizing 1,3,5,7-tetramethylcyclotetrasiloxane that is used in a chemical vapor deposition process against polymerization during extended periods of heating, the process comprising: providing a free radical scavenger to said 1,3,5,7-tetramethylcyclotetrasiloxane.

7. The process of claim 6 wherein said free radical scavenger is selected from the group consisting of 2,6-di-tert-butyl-4-methyl phenol, 2,2,6,6-tetramethyl-1-piperidinyloxy and mixtures thereof.

8. The process of claim 7 wherein said scavenger is provided in an amount of 50–500 ppm (vol.).

9. The process of claim 7 wherein said 2,2,6,6-tetramethyl-1-piperidinyloxy is provided in an amount of 50–230 ppm (vol.).

10. A process for stabilizing 1,3,5,7-tetramethylcyclotetrasiloxane against polymerization used in a chemical vapor deposition process for silicon oxides in electronic material fabrication comprising providing a neutral to weakly acidic polymerization inhibitor to said 1,3,5,7-tetramethylcyclotetrasiloxane and providing a free radical scavenger to said 1,3,5,7-tetramethylcyclotetrasiloxane.

11. The process of claim 10 wherein said inhibitor is selected from the group consisting of 2,4-pentanedione, 1-hexanoic acid, glycerol, acetic anhydride, less than 1% (vol.) 1,1,1,5,5,5-hexamethyltrisiloxane and mixtures thereof.

12. The process of claim 10 wherein said free radical scavenger is selected from the group consisting of 2,6-di-tert-butyl-4-methyl phenol, 2,2,6,6-tetramethyl-1-piperidinyloxy and mixtures thereof.

13. A composition of 1,3,5,7-tetramethylcyclotetrasiloxane, used in a chemical vapor deposition process as a precursor for silicon oxides in electronic material fabrication, stabilized against polymerization, comprising 1,3,5,7-tetramethylcyclotetrasiloxane and a neutral to weakly acidic polymerization inhibitor and a free radical scavenger.

14. A composition of 1,3,5,7-tetramethylcyclotetrasiloxane, used in a chemical vapor deposition process as a precursor for silicon oxides in electronic material fabrication, stabilized against polymerization, comprising (a) 1,3,5,7-tetramethylcyclotetrasiloxane, (b) a neutral to weakly acidic polymerization inhibitor selected from the group consisting of 2,4-pentanedione; 1-hexanoic acid; glycerol; acetic anhydride; less than 1% (vol.) 1,1,1,5,5,5-hexamethyltrisiloxane; less than 1% (vol.) 1,1,1,3,5,5,5-heptamethyltrisiloxane; β-diketones RC(O)CH$_2$C(O)R; aliphatic carboxylic acids RCOOH; aliphatic dicarboxylic acids HOOC—(CH$_2$)—COOH in which $1 \leq n \leq 8$; phenols C$_6$R$_{(6-n)}$(OH)$_n$ in which $1 \leq n \leq 5$; polyols CH$_2$X(CHX)$_n$CH$_2$X, in which X=H or OH but at least one X=OH and $1 \leq n \leq 8$; anhydrides RCH$_2$—C(O)—O—C(O)—CH$_2$R; hydrodosiloxanes R$_3$Si—(O—SiR$_2$)$_n$—OSiR$_3$, in which $0 \leq n \leq 8$, all wherein R is individually selected from the group consisting of hydrogen, normal, branched or cyclic C$_{1-10}$ alkyl groups; and mixtures thereof, and (c) a free radical scavenger selected from the group consisting of 2,6-di-tert-butyl-4-methyl phenol, 2,2,6,6-tetramethyl-1-piperidinyloxy, 2-tert-butyl-4-hydroxyanisole, 3-tert-butyl-4-hydroxyanisole, propyl ester 3,4,5-trihydroxy-benzonic acid, 2-(1,1-dimethylethyl)-1,4-benzenediol, diphenylpicrylhydrazyl, 4-tert-butylcatechol, N-methylaniline, p-methoxydiphenylamine, diphenylamine, N,N'-diphenyl-p-phenylenediamine, p-hydroxydiphenylamine, phenol, octadecyl-3-(3,5-di-tert-butyl-4-hydroxyphenyl)propionate, tetrakis(methylene(3,5-di-tert-butyl)-4-hydroxy-hydrocinnamate)methane, phenothiazines, alkylamidonoisoureas, thiodiethylene bis(3,5,-di-tert-butyl-4-hydroxy-hydrocinnamate, 1,2,-bis(3,5-di-tert-butyl-4hydroxyhydrocinnamoyl)hydrazine, tris(2-methyl-4-hydroxy-5-tert-butylphenyl)butane, cyclic neopentanetetrayl bis(octadecyl phosphite), 4,4'-thiobis(6-tert-butyl-m-cresol), 2,2'-methylenebis(6-tert-butyl-p-cresol), oxalyl bis(benzylidenehydrazide) and mixtures thereof.

15. A composition of 1,3,5,7-tetramethylcyclotetrasiloxane, used in a chemical vapor deposition process as a precursor for silicon oxides in electronic material fabrication, stabilized against polymerization, comprising 1,3,5,7-tetramethylcyclotetrasiloxane, and 2,4-pentanedione.

16. A composition of 1,3,5,7-tetramethylcyclotetrasiloxane, used in a chemical vapor deposition process as a precursor for silicon oxides in electronic material fabrication, stabilized against polymerization, comprising 1,3,5,7-tetramethylcyclotetrasiloxane, and 1-hexanoic acid.

17. A composition of 1,3,5,7-tetramethylcyclotetrasiloxane, used in a chemical vapor deposition process as a precursor for silicon oxides in electronic material fabrication, stabilized against polymerization, comprising 1,3,5,7-tetramethylcyclotetrasiloxane, and glycerol.

18. A composition of 1,3,5,7-tetramethylcyclotetrasiloxane, used in a chemical vapor deposition process as a precursor for silicon oxides in electronic material fabrication, stabilized against polymerization, comprising 1,3,5,7-tetramethylcyclotetrasiloxane, and acetic anhydride.

19. A composition of 1,3,5,7-tetramethylcyclotetrasiloxane, used in a chemical vapor deposition process as a precursor for silicon oxides in electronic material fabrication, stabilized against polymerization, comprising 1,3,5,7-tetramethylcyclotetrasiloxane, 2,4-pentanedione and a free radical scavenger selected from the group consisting of 2,6-di-tert-butyl-4-methyl phenol, 2,2,6,6-tetramethyl-1-piperidinyloxy and mixtures thereof.

20. A composition of 1,3,5,7-tetramethylcyclotetrasiloxane, used in a chemical vapor deposition process as a precursor for silicon oxides in electronic material fabrication, stabilized against polymerization, comprising 1,3,5,7-tetramethylcyclotetrasiloxane, 1-hexanoic acid and a free radical scavenger selected from the group consisting of 2,6-di-tert-butyl-4-methyl phenol, 2,2,6,6-tetramethyl-1-piperidinyloxy and mixtures thereof.

21. A composition of 1,3,5,7-tetramethylcyclotetrasiloxane, used in a chemical vapor deposition process as a precursor for silicon oxides in electronic material fabrication, stabilized against polymerization, comprising 1,3,5,7-tetramethylcyclotetrasiloxane, glycerol and a free radical scavenger selected from the group consisting of 2,6-di-tert-butyl-4-methyl phenol, 2,2,6,6-tetramethyl-1-piperidinyloxy and mixtures thereof.

22. A composition of 1,3,5,7-tetramethylcyclotetrasiloxane, used in a chemical vapor deposition process as a precursor for silicon oxides in electronic material fabrication, stabilized against polymerization, comprising 1,3,5,7-tetramethylcyclotetrasiloxane, acetic anhydride and a free radical scavenger selected from the group consisting of 2,6-di-tert-butyl-4-methyl phenol, 2,2,6,6-tetramethyl-1-piperidinyloxy and mixtures thereof.

23. A composition of 1,3,5,7-tetramethylcyclotetrasiloxane comprising (a) 1,3,5,7-tetramethylcyclotetrasiloxane, (b) a polymerization inhibitor selected from 2,4-pentanedione; 1-hexanoic acid; glycerol; acetic anhydride; β-diketones $RC(O)CH_2C(O)R$; aliphatic carboxylic acids RCOOH; aliphatic dicarboxylic acids $HOOC-(CH_2)_n-COOH$ in which $1 \leq n \leq 8$; phenols $C_6R_{(6-n)}(OH)_n$ in which $1 \leq n \leq 5$; polyols $CH_2X(CHX)_nCH_2X$, in which X=H or OH but at least one X=OH and $1 \leq n \leq 8$; anhydrides $RCH_2-C(O)-O-C(O)-CH_2R$; hydrodosiloxanes $R_3Si-(O-SiR_2)_n-OSiR_3$, in which $0 \leq n \leq 8$, all wherein R is individually selected from the group consisting of hydrogen, normal, branched or cyclic $C_{1-10}$ alkyl groups; and mixtures thereof, and (c) a free radical scavenger selected from 2,6-di-tert-butyl-4-methyl phenol, 2,2,6,6-tetramethyl-1-piperidinyloxy, 2-tert-butyl-4-hydroxyanisole, 3tert-butyl-4-hydroxyanisole, propyl ester 3,4,5-trihydroxy-benzoic acid, 2-(1,1-dimethylethyl)-1,4-benzenediol, diphenylpicrylhydrazyl, 4-tert-butylcatechol, N-methylaniline, p-methoxydiphenylamine, diphenylamine, N,N'-diphenyl-p-phenylenediamine, p-hydroxydiphenylamine, phenol, octadecyl-3(3,5-di-tert-butyl-4-hydroxyphenyl)propionate, tetrakis(methylene(3,5-di-tert-butyl)-4-hydroxyhydrocinnamate)methane, phenothiazines, alkylamidonoisoureas, thiodiethylene bis(3,5-di-tert-butyl-4-hydroxy-hydrocinnamate, 1,2,-bis(3,5-di-tert-butyl-4-hydroxyhydrocinnamoyl)hydrazine, tris(2-methyl-4-hydroxy-5-tert-butylphenyl)butane, cyclic neopentanetetrayl bis(octadecyl phosphite), 4,4'-thiobis(6-tert-butyl-m-cresol), 2,2'-methylenebis(6-tert-butyl-p-cresol), oxalyl bis(benzylidenehydrazide) and mixtures thereof.

24. A composition of a cyclotetrasiloxane, the composition comprising; (a) said cyclotetrasiloxane having the following formula:

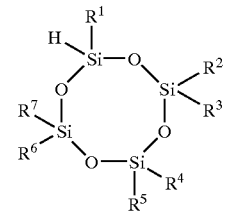

where $R^{1-7}$ are individually selected from the group consisting of hydrogen, a normal, branched or cyclic $C_{1-10}$ alkyl group, and a $C_{1-4}$ alkoxy group, (b) a neutral to weakly acidic polymerization inhibitor; and (c) a free radical scavenger.

25. A composition that is used in a chemical vapor deposition process and is stabilized for extended periods of heating, the composition comprising:

(a) a cyclotetrasiloxane having the following formula:

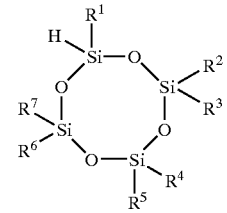

where $R^{1-7}$ are individually selected from the group consisting of hydrogen, a normal, branched or cyclic $C_{1-10}$ alkyl group, and a $C_{1-4}$ alkoxy group; and (b) a free radical scavenger.

26. The composition of claim 25 wherein the free radical scavenger is at least one selected from 2,6-di-tert-butyl-4-methyl phenol, 2,2,6,6-tetramethyl-1-piperidinyloxy, 2-tert-butyl-4-hydroxyanisole, 3-tert-butyl-4-hydroxyanisole, propyl ester 3,4,5-trihydroxy-benzoic acid, 2-(1,1-dimethylethyl)-1,4-benzenediol, diphenylpicrylhydrazyl, 4-tert-butylcatechol, N-methylaniline, p-methoxydiphenylamine, diphenylamine, N,N'-diphenyl-p- phenylenediamine, p-hydroxydiphenylamine, phenol, octadecyl-3-(3,5-di-tert-butyl-4-hydroxyphenyl)propionate, tetrakis(methylene(3,5-di-tert-butyl)-4-hydroxy-hydrocinnamate)methane, phenothiazines, alkylamidonoisoureas, thiodiethylene bis(3,5,-di-tert-butyl-4-hydroxy-hydrocinnamate 1,2,-bis(3,5-di-tert-butyl-4-hydroxyhydrocinnamoyl)hydrazine, tris(2-methyl-4-hydroxy-5-tert-butylphenyl)butane, cyclic neopentanetetrayl bis(octadecyl phosphite), 4,4'-thiobis(6-tert-butyl-m-cresol), 2,2'-methylenebis(6-tert-butyl-p-cresol), oxalyl bis(benzylidenehydrazide), raw seed oils, wheat germ oils, tocopherols, and gums.

27. A composition of 1,3,5,7-tetramethylcyclotetrasiloxane, used in a chemical deposition process and stabilized for extended periods of heating, comprising 1,3,5,7-tetramethylcyclotetrasiloxane and at least one free radical scavenger selected from the group consisting of 2,6-di-tert-butyl-4-methyl phenol, 2,2,6,6-tetramethyl-1-piperidinyloxy, and mixtures thereof.

28. A process for stabilizing a cyclotetrasiloxane for extended periods of heating wherein the cyclotetrasiloxane is used as a precursor in a chemical vapor deposition process and has the following formula:

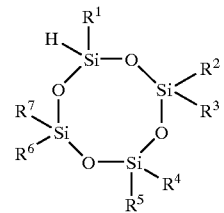

where $R^{1-7}$ are individually selected from the group consisting of hydrogen, a normal, branched or cyclic $C_{1-10}$ alkyl group, and a $C_{1-4}$ alkoxy group, the process comprising: adding a free radical scavenger to the cyclotetrasiloxane.

* * * * *

UNITED STATES PATENT AND TRADEMARK OFFICE
CERTIFICATE OF CORRECTION

PATENT NO.    : 6,858,697 B2
DATED         : February 22, 2005
INVENTOR(S)   : Steven Gerard Mayorga, Manchao Xiao and Thomas Richard Gaffney It is certified that error appears in the above-identified patent and that said Letters Patent is hereby corrected as shown below:

Column 16,
Line 50, delete "3,4,5-trihydroxy-benzonic" and substitute therefore -- 3,4,5-trihydroxy-benzoic --

Column 18,
Line 4, delete "tree" and substitute therefore -- free --

Signed and Sealed this

Tenth Day of May, 2005

JON W. DUDAS
*Director of the United States Patent and Trademark Office*